United States Patent
Pacheco Da Cunha

(10) Patent No.: US 8,677,845 B2
(45) Date of Patent: Mar. 25, 2014

(54) MEASUREMENT PENDULUM FOR STORED GRAINS

(76) Inventor: Otalicio Pacheco Da Cunha, Sao Leopolda (BR)

( * ) Notice: Subject to any disclaimer, the term of this patent is extended or adjusted under 35 U.S.C. 154(b) by 358 days.

(21) Appl. No.: 13/122,218

(22) PCT Filed: Oct. 16, 2009

(86) PCT No.: PCT/BR2009/000348
§ 371 (c)(1),
(2), (4) Date: Apr. 1, 2011

(87) PCT Pub. No.: WO2010/043015
PCT Pub. Date: Apr. 22, 2010

(65) Prior Publication Data
US 2011/0174072 A1    Jul. 21, 2011

(30) Foreign Application Priority Data
Oct. 17, 2008  (BR) ...................................... 0804668

(51) Int. Cl.
*G01N 33/00* (2006.01)
(52) U.S. Cl.
USPC .......................................................... 73/866

(58) Field of Classification Search
USPC ............................................................ 73/866
See application file for complete search history.

(56) References Cited

U.S. PATENT DOCUMENTS

| 6,440,475 B1 | 8/2002 | McNeff et al. |
| 6,986,294 B2 * | 1/2006 | Fromme et al. ............... 73/865.8 |
| 8,410,945 B2 * | 4/2013 | Breed ............................ 340/601 |
| 2003/0033862 A1 | 2/2003 | McElhaney et al. |
| 2005/0080567 A1 * | 4/2005 | Wieting et al. .................... 702/2 |

FOREIGN PATENT DOCUMENTS

| BG | 64608 B1 | 8/2005 |
| EP | 0518752 A1 | 12/1992 |

* cited by examiner

*Primary Examiner* — Hezron E Williams
*Assistant Examiner* — Rodney T Frank
(74) *Attorney, Agent, or Firm* — Zarley Law Firm, P.L.C.

(57) ABSTRACT

A measurement pendulum for stored grains mass in which a pendulum type measurer (1) formed by a protection structure (2), holds sensors (3) in its inside that have the direct interface with the outside through one or more transversal passages (4), provided of a porous protection (5) in order to measure the desired variables from the interstitial air that crosses the porous protection (5), and represents the grains characteristics in the outside.

19 Claims, 3 Drawing Sheets

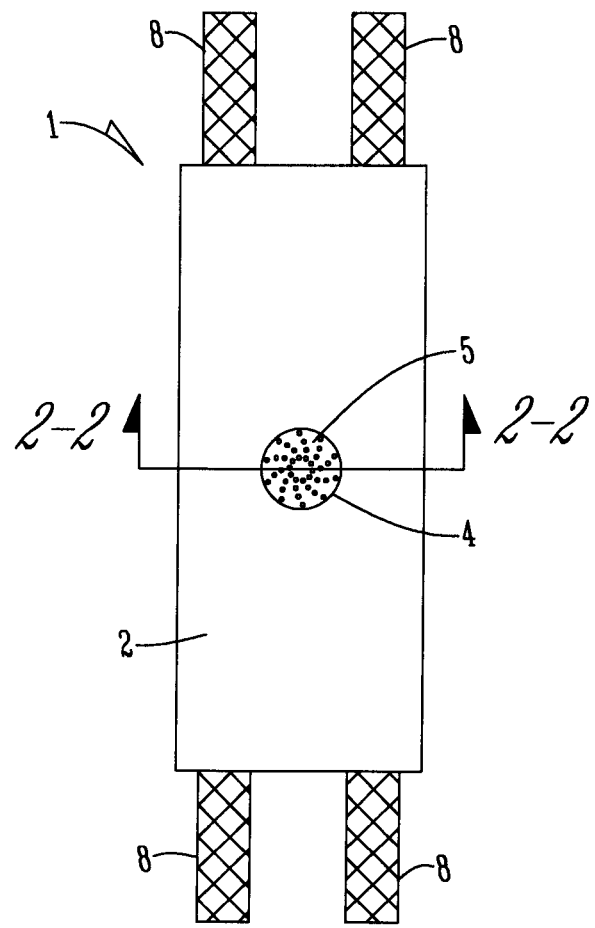
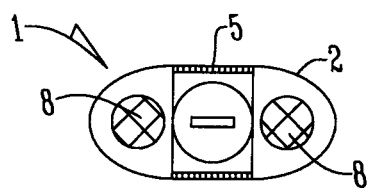

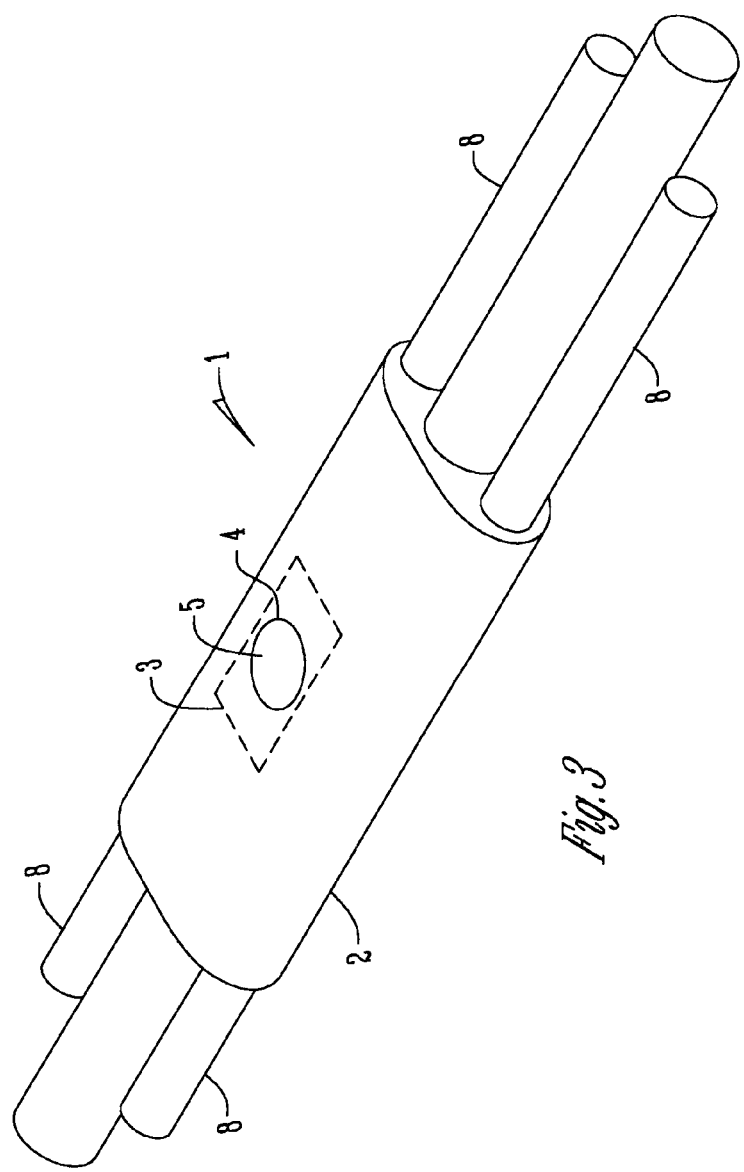

MEASUREMENT PENDULUM FOR STORED GRAINS

BACKGROUND OF THE INVENTION

The present invention belongs, in a general way, to the technological sector of equipment for psychometrics, used for performing measurements in the mass of grains (6) stored in horizontal and vertical silos (also known as a grain storage device (7)), and refers, more specifically to a new conception applied to a pendulum type measurer (1) that is hung on steel cables (8) and immersed in the grains mass 6, measuring the temperature, relative humidity, and their dew point temperature.

The state of art of this technological sector is made of thermometry temperature sensors that can be based on the thermocouple principle or other conventional ones, positioned inside a pendulum of resistant material held by two steel cables (9), immersed in the mass of grain to measure the temperature on different points of this mass.

The conventional sensors, already comprised by the state of technique, measure the temperature inside a cable on a first moment, suffering interferences of intractable convections, afterwards measuring, through conduction and heat transfer, the temperature of the grains that are in contact with the external surface of the pendulum. This measured temperature refers to a small portion of grains (approximately 0.2 kg), because the grains present a high thermal insulation, as mentioned in different technical literatures, one centimeter thickness of a corn grain (1 cm) is equivalent to a concrete wall of twelve centimeters (12 cm). Because of this characteristic inherent to grains, we have an approximate measurement of their temperature, which makes the storage system a high risk process, subject to irreversible losses of dry matter due to the attack of fungi, insects, and bacteria.

SUMMARY OF THE INVENTION

The proposed invention views to optimize significantly, and with precision the measures (parameters) of interstitial temperature (.degree. C.) and relative humidity (% r.h.) performed with the system of psychrometry of silos and grain deposits, reducing the grain losses due to the attack of fungi, insects, and bacteria.

This objective will be reached through a new conception applied to a measurement pendulum, that holds temperature (.degree. C.), relative humidity (% r.h.), and dew point temperature (.degree. C. d.p.), the novelty being in the introduction of a transversal passage with a porous protection, which enables to measure with precision (with at least three figures after the point) the interstitial air, which represents the actual characteristics of grains storage, and provides much more precise and trustful results for the analysis, including of trends.

BRIEF DESCRIPTION OF THE DRAWINGS

It must be understood, by any one who knows the subjects that the objective of the presented drawings is not to be limitative to the protected matter, just in the revealed concretizations. These are just explanatory of the implementations considered more efficient by the inventor, but any other construction that is within the same inventive scope is also protected.

So that the invention in view, revealed in this descriptive report, can be fully understood and taken to practice by any technician of this technological sector, it will be explained in a clear, concise, and sufficient form, having as basis the drawings annexed and listed herein below.

FIG. 1, front elevation view drawing of the proposed measurer, in which is indicated a cut AA.

FIG. 2, top elevation sectional view of the cut AA indicated in the previous figure.

FIG. 3, perspective view drawing of the measurer of FIGS. 1 and 2.

DETAILED DESCRIPTION OF THE PREFERRED EMBODIMENT OF THE INVENTION

Figure 4:
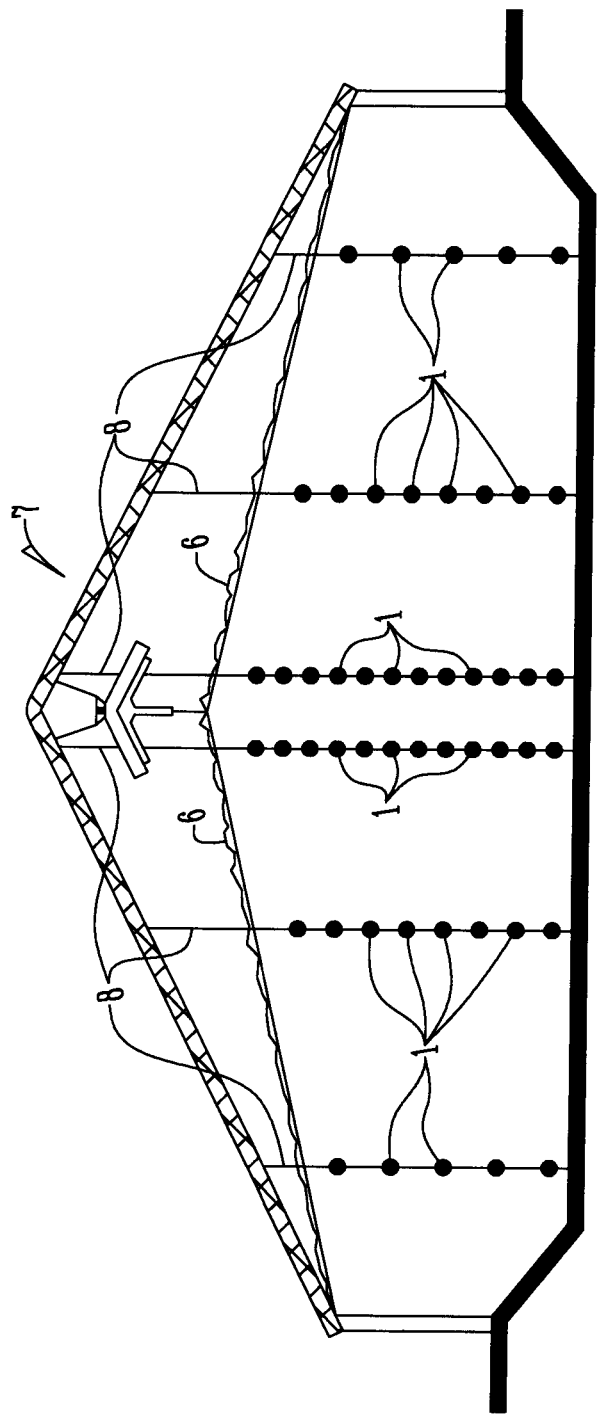
FIG. 4, elevation view of a grain storage device holding a mass of stored grains, a plurality of cables hung from the grain storage device with pendulum type measurers hung from the cables and immersed in the mass of stored grains to measure parameters of the mass of stored grains such as temperature, humidity and due point.

The betterment on a measurement pendulum for stored grains mass, object of this descriptive report, refers to a pendulum type measurer (1), formed by a protection structure (2), made of any material with adequate resistance to support the forces within the stored grains mass (6) stored within grain storage device (7) and hung by cable (8) that holds sensors (3) of temperature (.degree. C.), relative humidity (% r.h), and dew point temperature (.degree. C. d.p.) in its inside, or of any other variable desired of grains mass (6), in which the direct interface of the mentioned sensors (3) with the outside is made by one or more transversal passages (4) provided with porous protection (5), so that the sensor (3) measures the variables desired of the interstitial air, which crosses the porous protection (5) and represents the actual characteristics of the grains in the outside.

It must be clear for any expert in the technique that the invention is not just restricted to the preferential construction illustrated in the annexed figures. The pendulum (1) can have various transversal passages (5) that may present innumerable forms (round, oval, square, rectangular, and others), as well as the porous protection (5), which is not limited to this preferential construction, being possible to adopt a tubular form around the sensor (3), involve the cable, or present smaller holes (4) that constructively do not need protection.

In the present descriptive report was dealt about an invention with industrial application, with inventive novelty and activity, presenting all requirements demanded by law to receive the required privilege.

What is claimed is:

1. A pendulum type measurer for measuring parameters of stored grains within a grain storage device, comprising:
    a protection structure having an outside surface that forms an outer housing of the pendulum type measurer;
    a sensor positioned within and held by the protection structure;
    a transversal passage in the protection structure;
    wherein the sensor is positioned to interface with the transversal passage in the protection structure such that the sensor measures air variables outside the protection structure which represent characteristics of the stored grains.

2. The pendulum type measurer of claim 1 further comprising a porous member placed over the transversal passage.

3. The pendulum type measurer of claim 1, wherein the sensor is enclosed a combination of the protection structure and a tubular porous protection positioned over the transversal passage.

4. The pendulum type measurer of claim 1 wherein the transversal passage has one or openings dimensions that do not allow the grains passage there through so as to keep the sensor separated from the grain.

5. The pendulum type measurer of claim 1 wherein the transversal passage extends through a forward side and a rearward side of the protection structure.

6. The pendulum type measurer of claim 1 wherein the transversal passage extends laterally through a forward side and a rearward side of the protection structure, and a first porous member covers the transversal passage in the forward side, and a second porous member covers the transversal passage in the rearward side.

7. The pendulum type measurer of claim 1 wherein the protection structure provides resistance to forces within the stored grains and thereby protects the sensor positioned within the protection structure from damage by the grains.

8. The pendulum type measurer of claim 1 wherein the protection structure is formed of a tubular form around the sensor.

9. The pendulum type measurer of claim 1 wherein the protection structure is supported by at least one cable.

10. The pendulum type measurer of claim 1 wherein the protection structure is supported by a pair of cables.

11. The pendulum type measurer of claim 1 wherein the protection structure is supported by at least one cable that extends through the protection structure.

12. The pendulum type measurer of claim 1 wherein the protection structure is supported by a pair of cables that extends through the protection structure and connect to the grain storage device.

13. The pendulum type measurer of claim 1 wherein the sensor measures temperature of the stored grains.

14. The pendulum type measurer of claim 1 wherein the sensor measures humidity of the stored grains.

15. The pendulum type measurer of claim 1 wherein the sensor measures dew point of the stored grains.

16. The pendulum type measurer of claim 1 wherein the sensor measures temperature and humidity of the stored grains.

17. The pendulum type measurer of claim 5 wherein the pendulum type measurer remains stationary within the stored grains by supporting cables.

18. A pendulum type measurer for measuring parameters of stored grains within a grain storage device, comprising:
 a grain storage device;
 a mass of grains stored within the grain storage device;
 at least one cable hung from the grain storage device;
 the pendulum type measurer connected to the at least one cable and immersed in the mass of grains;
 the pendulum type measurer comprising:
  a protection structure having an outside surface that forms an outer housing of the pendulum type measurer;
  a sensor positioned within and held by the protection structure;
  a transversal passage in the protection structure;
  wherein the sensor is positioned to interface with the transversal passage in the protection structure such that the sensor measures variables outside the protection structure which represent characteristics of the stored grains including temperature and humidity.

19. The pendulum type measurer of claim 18 further comprising a porous member placed over the transversal passage.

* * * * *